US00PP08196P

United States Patent [19]

Bradford et al.

[11] Patent Number: Plant 8,196

[45] Date of Patent: Apr. 6, 1993

[54] NECTARINE TREE (WESTERN RED)

[76] Inventors: Lowell G. Bradford, 12439 E. Savana Rd.; Norman G. Bradford, 11875 E. Savana Rd., both of Le Grand, Calif. 95333

[21] Appl. No.: 833,068

[22] Filed: Feb. 10, 1992

[51] Int. Cl.[5] ..... A01H 5/00

[52] U.S. Cl. ..... Plt./41.1

[58] Field of Search ..... Plt./41.1

[56] References Cited

U.S. PATENT DOCUMENTS

P.P. 5,454 4/1985 Bradford ..... Plt. 41.1

P.P. 6,363 11/1988 Bradford ..... Plt. 41.1

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described approximately the third week in August, with first picking on Aug. 21, 1991. The fruit is uniformly large in size, excellent in flavor, attractively globose in shape, clingstone in type, very firm in texture, and almost full red in skin color. The variety was developed as a hybridized seedling with Red Diamond Nectarine (U.S. Plant Pat. No. 3,165) as the selected seed parent and May Diamond Nectarine (U.S. Plant Pat. No. 5,454) as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Western Red". The present variety was hybridized in 1986 by us in a cultivated area of our experimental orchard at Bradford Farms near Le Grand, Calif. in Merced County (San Joaquin Valley). It was developed by crossing the selected seed parent, Red Diamond Nectarine (U.S. Plant Pat. No. 3,165), with the selected pollen parent, May Diamond Nectarine (U.S. Plant Pat. No. 5,454). Subsequent to origination of the present variety of nectarine tree, we asexually reproduced it by budding and grafting, and such reproduction of plant and fruit characteristics were true to the original plant in all respects.

The fruit produced by the present variety is most similar to its seed parent, August Red Nectarine (U.S. Plant Pat. No. 6,363), by producing clingstone fruit that is very firm in texture and late season in maturing, but is distinguished therefrom and an improvement thereon by producing fruit that is larger in size, has a higher percentage of red color, and that ripens 7 to 10 days earlier.

The present variety is similar to its pollen parent, the May Diamond Nectarine (U.S. Plant Pat. No. 5,454), by producing high colored fruit that is very firm, but is very distinguished therefrom by producing fruit that is clingstone instead of freestone and that ripens approximately 75 days later.

DRAWING

The accompanying photograph exhibits four whole fruits positioned to display the charcteristics of the skin color and form, a sectioned half fruit divided transverse to the suture plane to reveal the flesh and stone, and representative leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard eating ripe on Aug. 25, 1991. All major color code designations are by reference to the Inter-Society Color Council, National Bureau of Standards. Common color names are also used occasionally.

TREE

Size: Large.
Vigor: Vigorous.
Growth: Upright and dense.
Form: Vase formed.
Hardiness: Hardy.
Production: Very productive.
Bearing: Regular bearer.
Trunk:
- *Size.*—Medium.
- *Texture.*—Medium.
- *Bark color.*—Grayish brown [61. gy.Br.].
- *Lenticels.*—Numerous. Color: Brownish gray [64. brGy]. Size: ⅛" to 3/16" [3.2 to 4.8 mm.].

Branches:
- *Size.*—Medium.
- *Texture.*—Medium.
- *Color.*—1st year wood topside: Grayish red [19. gy.R]. 1st year wood underside: Brilliant yellow green [116. brill.YG]. Older wood: Moderate brown [58. m.Br].
- *Lenticels.*—Numerous, very small.

Leaves:
- *Size.*—Large. Average length: 5¾" [146.1 mm.]. Average width: 1¾" [44.5 mm.].
- *Thickness.*—Medium.
- *Form.*—Elliptical.
- *Apex.*—Acuminate.
- *Base.*—Acute.

*Surface.*—Smooth.

*Color.*—Dorsal surface: Moderate olive green [125. m. OlG]. Ventral surface: Moderate yellow green [120. m.YG].

*Margin.*—Finely serrate.

*Venation.*—Pinnately net veined.

*Petiole.*—Average length: ½" [12.7 mm.]. Average thickness: 1/16" [1.6 mm.]. Color: Light yellow green [119. 1.YG].

*Stipules.*—Numerous. Average length: ¼" [6.4 mm.].

*Glands.*—Average number: mostly 2 to 4 per leaf. Position: Some oppositely and some alternately positioned on petiole and base of blade. Size: Small. Form: Reniform. Color: Moderate yellow green [120. m.YG].

Flower buds:

*Hardiness.*—Hardy.

*Size.*—Medium.

*Length.*—Medium.

*Form.*—Free.

*Surface.*—Pubescent.

Flowers:

*Blooming period.*—Medium as compared with other varieties.

*Size.*—Small.

*Color.*—Moderate pink [5. m.Pk].

FRUIT

Maturity when described: Hard, but eating ripe, Aug. 25, 1991.

Date of first picking: Aug. 21, 1991.

Date of last packing: Sep. 4, 1991.

Size: Uniform, large.

*Average diameter axially.*—2⅝" [66.7 mm.].

*Average traversely in suture plane.*—2½" [63.5 mm.].

Form: Uniform, symmetrical, globose.

*Longitudinal section form.*—Round to slightly oblong.

*Transverse section through diameter.*—Round.

Suture: An inconspicuous shallow line near the base becoming a shallow groove near the apex, extending from the base to slightly beyond the apex, with a slight depression beyond the pistil point.

Ventral surface: Rounded, lipped toward the apex.

Lips: Slightly unequal.

Cavity: Flaring, slightly elongated in the suture plane, with the suture showing on one side.

*Depth.*—½" [12.7 mm.].

*Breadth.*—⅞" [22.2 mm.].

Base: Rounded to slightly truncate, with stem markings typical.

Apex: Rounded.

Pistil point: Mostly oblique, negligible in length, depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed as of yet.

*Color.*—Very dark red [17. v.d.R] over a deep reddish orange [36. deep rO] background with some brilliant yellow [83. brill.Y] flecking.

Flesh:

*Color.*—Brilliant yellow [83. brill.Y] with dark red [16. d.R] streaking most prevalent near the stone.

*Amygdalin.*—Moderate.

*Juice.*—Abundant, rich.

*Texture.*—Very firm, very crisp.

*Fibers.*—Abundant, fine.

*Ripens.*—Slightly earlier at the base and along the lips.

*Flavor.*—Sweet and slightly acidic.

*Aroma.*—Moderate.

*Eating quality.*—Very good.

STONE

Type: Clingstone.

Form: Oblong.

Base: Slightly oblique.

Apex: Acute.

Sides: Equal.

Surface: Furrowed toward the apex and pitted toward the base.

Ridges: Jagged toward the base.

Color: Light brown [57. .Br].

Pit wall: 5/16" [7.9 mm.] thick.

Tendency to split: None observed.

Kernel:

*Form.*—Oval.

*Taste.*—Sweet.

*Viable.*—Yes.

*Average width.*—½" [12.7 mm.].

*Average length.*¾" [19.1 mm.].

*Color.*—light yellow [86. .Y] when first cracked.

*Pellicle color.*—Grayish yellowish brown [80. gy-.yBr].

*Amygdalin.*—Scant.

USE

Market: Fresh and long distance shipping.

Keeping quality: Excellent.

Shipping quality: Excellent.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is most similar to its seed parent, August Red Nectarine (U.S. Plant Pat. No. 6,363), by producing clingstone fruit that is very firm in texture and late season in maturing, but is distinguished therefrom and an improvement thereon by producing fruit that is larger in size, has a higher percentage of red color, and that ripens 7 to 10 days earlier.

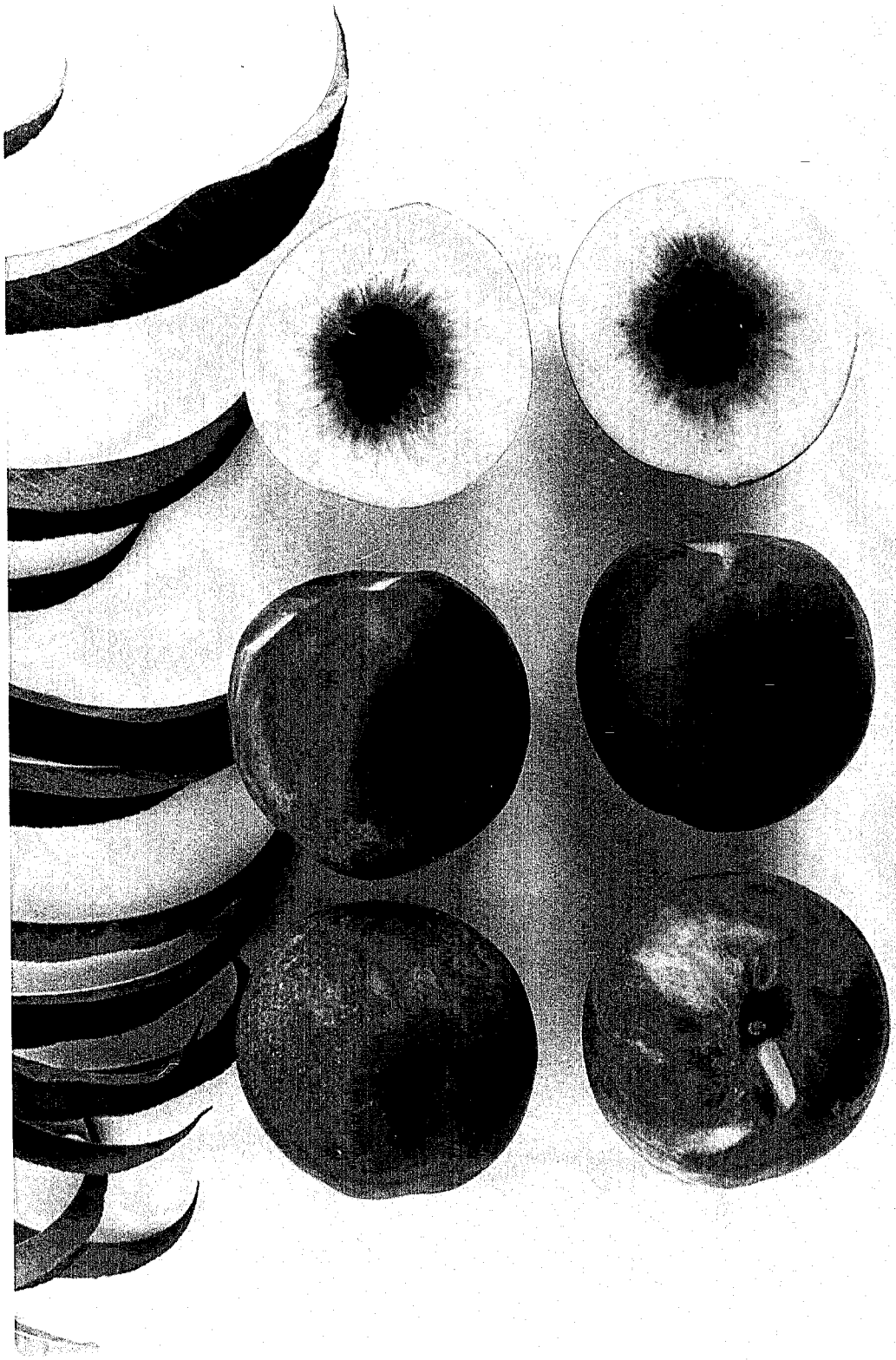

* * * * *